United States Patent [19]

Johnson

[11] 4,339,831
[45] Jul. 20, 1982

[54] DYNAMIC ANNULUS HEART VALVE AND RECONSTRUCTION RING

[75] Inventor: Keith M. Johnson, Coon Rapids, Minn.

[73] Assignee: Medtronic, Inc., Minneapolis, Minn.

[21] Appl. No.: 248,624

[22] Filed: Mar. 27, 1981

[51] Int. Cl.³ .............................................. A61F 1/22
[52] U.S. Cl. ..................................... 3/1.5; 137/512.15; 137/854
[58] Field of Search ...................... 3/1.5, 1; 137/512.1, 137/512.15, 854, 852

[56] References Cited

U.S. PATENT DOCUMENTS

| | | | |
|---|---|---|---|
| 2,682,057 | 6/1954 | Lord | 3/1.5 |
| 2,832,078 | 4/1958 | Williams | 3/1.5 |
| 2,859,771 | 11/1958 | Blagg | 137/512.15 |
| 3,022,796 | 2/1962 | Cummings | 137/854 X |
| 3,113,586 | 12/1963 | Edmark | 137/512.1 |
| 3,320,972 | 5/1967 | High et al. | 137/844 |
| 3,416,562 | 12/1968 | Freeman | 3/1.5 X |
| 3,548,417 | 12/1970 | Kischer | 3/1.5 |
| 3,579,642 | 5/1971 | Heffernan et al. | 3/1.5 |
| 3,608,097 | 9/1971 | Bellhouse et al. | 3/1.5 |
| 3,628,535 | 12/1971 | Ostrowsky et al. | 3/1.5 X |
| 3,671,979 | 6/1972 | Moulopoulos | 3/1.5 |
| 3,689,942 | 9/1972 | Rapp | 3/1.5 |
| 3,736,598 | 6/1973 | Bellhouse et al. | 3/1.5 |
| 3,739,402 | 6/1973 | Cooley et al. | 3/1.5 |
| 3,898,701 | 8/1975 | La Russa | 3/1.5 |
| 4,056,854 | 11/1977 | Boretos et al. | 3/1.5 |
| 4,192,020 | 3/1980 | Davis et al. | 3/1.5 |
| 4,218,782 | 8/1980 | Rygg | 3/1.5 |
| 4,218,783 | 8/1980 | Reul et al. | 3/1.5 |

OTHER PUBLICATIONS

"An Inverted Tricuspid Plastic Mitral Valve" by R. W. Ernst et al., The Journal of Thoracic & Cardiovascular Surgery, vol. 46, No. 6, Dec. 1963, pp. 737–743.
Prosthetic Heart Valves (Book), Lyman A. Brewer III—Editor-in-Chief, Charles C. Thomas—Publisher, Springfield, Ill., 1969, pp. 262–277.

Primary Examiner—Ronald L. Frinks
Attorney, Agent, or Firm—Joseph F. Breimayer; John L. Rooney; Carl A. Forest

[57] ABSTRACT

A synthetic leaflet aortic and mitral heart valve for use in replacement of diseased natural heart valves having a flexible, curved framework, a flexible membrane attached to the framework and fixation means for attaching the valve to the tissue annulus. The framework consists of at least three curved flexible valve struts, each joined together at one end to a common central point of the valve and extending in the same direction radially at equal angles so that the free ends are unattached and at a distance from one another. The free ends are provided with sewing pads for artificial attachment of each free end separately to the natural tissue annulus or to an artificial annulus reconstruction ring which itself is sutured to the tissue annulus to restore its symmetry. The membrane is formed of a thin, common flexible synthetic material which is hemispherically shaped to fit over, and be attached to the framework to provide at least three partial hemispheric segments extending between adjacent frame struts in such a manner that the free edge of each segment can contact the tissue annulus when the valve is closed. Upon forward flow of the blood, the valve segments collapse inward against one another and allow blood to pass between the tissue annulus and the collapsed membrane segments.

19 Claims, 8 Drawing Figures

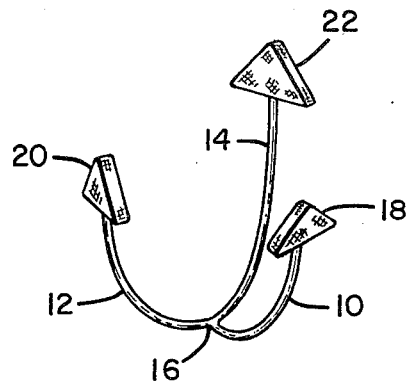
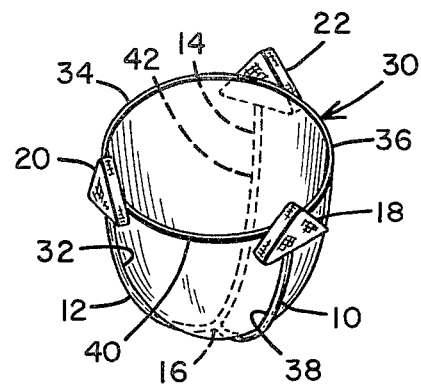
Fig. 1     Fig. 2
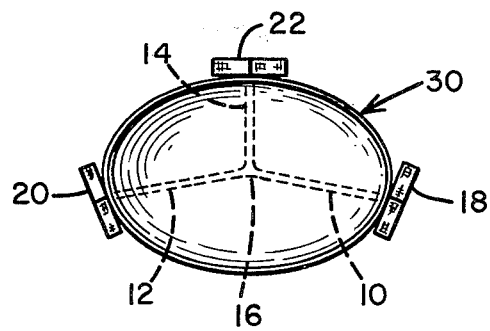
Fig. 3
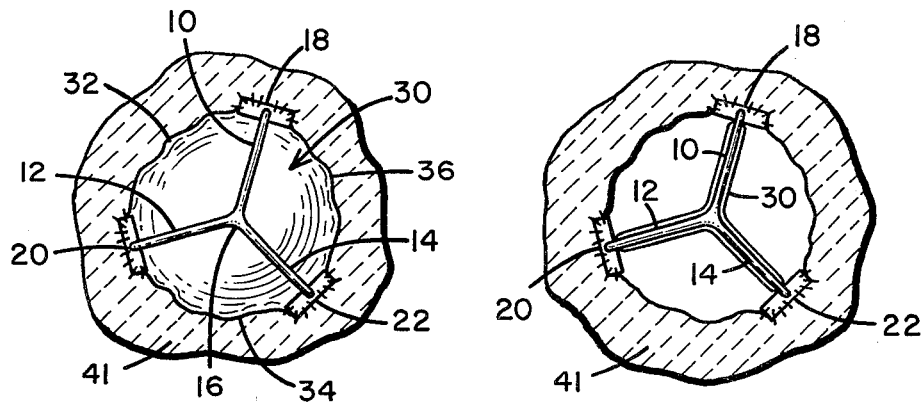
Fig. 4     Fig. 5

DYNAMIC ANNULUS HEART VALVE AND RECONSTRUCTION RING

BACKGROUND OF THE INVENTION

1. Field of the Invention

This invention relates to a synthetic leaflet aortic or mitral heart valve prosthesis.

2. Description of the Prior Art

Prosthetic heart valves have many forms and designs and have been used for more than 20 years for treatment of heart patients when replacement of a diseased natural valve or malfunctioning prosthesis is the treatment of choice. Although prosthetic valves have been made in numerous configurations and from many different materials, none has been found to answer all of the requirements for durability, biocompatability, nonthrombogenicity and hemodynamic excellence. Basically, there are two types of heart valve prostheses: mechanical valve prostheses and natural tissue valve prostheses. Mechanical valves, although very durable and hemodynamically acceptable (in some forms), have proven to be thrombogenic. Tissue valves, on the other hand, are relatively nonthrombogenic but exhibit relatively poor hemodynamics and questionable durability.

Other heart valves have been designed using synthetic materials in configurations similar to the natural tissue valves and in other dissimilar configurations. The heart valve shown in U.S. Pat. No. 2,832,078, for example, employs sacs or membrane sections of polyfluoroethylene mounted within a stainless steel tubular frame, the sacs filling upon closure of the valve and collapsing outwardly and against the steel frame when the flow or pressure of blood is reversed. A similarly functioning valve design, employing terylene-silicone rubber synthetic materials, is shown in U.S. Pat. No. 3,736,598. Heart valves of these configurations require an outer ring structure against which the sac-like membranes collapse upon opening of the valve.

Further membrane valves structures for temporary use are shown in the U.S. Pat. Nos. 3,671,979 and 4,056,854. The design of the first cited patent employs an umbrella shaped membrane wherein in the apex of the umbrella resides in the vessel in the direction in which the flow of blood is to be prevented, and the apex is affixed at or near the distal end of a flexible catheter so that the catheter and umbrella membrane may be placed in a blood vessel in proximity to the natural valve. In operation, the membrane of the valve callapses and folds against the catheter to permit the flow of blood in the proper direction between the centrally disposed catheter and the vessel wall, and when flow in that direction ceases and flow starts in the reverse direction, the force of the blood flow is supposed to cause the membrane to open so that the free edge of the valve membrane contacts the inner wall of the vessel to occlude the vessel to further reversed flow of blood.

The artificial heart valve design of the U.S. Pat. No. 4,056,854 is again a valve supported at the end of a catheter and consists of a tubular, sac-like membrane attached at one end to a ring metallic support of a springing material which is supported by the catheter in contact with the blood vessel wall. Fow of the blood in the proper direction causes the membrane to open against the downstream surface of the blood vessel wall, and reverse blood pressure causes the free end of the membrane to collapse inward against itself and against the catheter to stop blood flow.

These catheter mounted valve designs are not suited for permanent implantation in a tissue annulus for permanent replacement of the diseased or defective heart valve and can only be used temporarily in blood vessels. Mitral placement of these valves would not be possible and aortic placement would not be efficient. A further problem arises from the use of a catheter support which provides areas of downstream blood stagnation which could increase the incidence of thrombus formation leading to reduction of a valving action and possible fatal thromboembolic complications.

A further heart valve design is depicted in U.S. Pat. No. 3,898,701 which also employs an open sac-like silicone rubber or plastic membrane with one end supported by a ring sutured to the valve annulus. A central disposed separator is necessary to prevent inversion of the free end of the membrane. This design suffers from the necessity of an outer ring and separator which can lead to thrombus formation.

The various designs of heart valve prostheses employing synthetic materials all suffer to one degree or another, either from the material employed or the design configuration, from the incidence of thrombus formation. Furthermore, the designs that have found widespread medical acceptance also employ rigid or semi-rigid valve ring structures which do not enjoy the ability to flex or move with the movement of the tissue annulus as the heart expands and contracts, reducing myocardial efficiency and leading to perivalvular leaks and valvular dehiscence in a significant number of patients. In addition, the ring structures occupy up to 50 percent of the available annular area for blood flow, thus reducing cardiac efficiency and raising transvalvular pressure gradients.

SUMMARY OF THE INVENTION

This invention provides a dynamic annulus heart valve configuration which may effectively provide the non-thrombogenic qualities of tissue valves while not sacrificing durability or hemodynamic performance. The dynamic annulus valve incorporates a flexible framework of suitable materials to which is attached a synthetic, flexible membrane for effecting closure of the valve, and fixation means for attaching the valve to the tissue annulus. The framework comprises a plurality of curved flexible valve struts, each joined together at one end to a common central point of the valve and extending radially so that the free ends are unattached and terminate at a distance from one another. The structural extremities or free ends are provided with sewing pads for attachment of each extremity separately to the natural tissue annulus. The membrane is formed of a thin, flexible synthetic material which is shaped in an approximately hemispheric or paraboloid form to fit over, and be attached to, the framework to provide at least three partial hemispheric segments extending between adjacent frame struts in such a manner that the free edge of each segment can contact the tissue annulus when the valve is closed.

Fixation of the valve to the patient is accomplished by placing sutures through the sewing pads on the three structural extremities of the valve strut flexible frames. In the event that the tissue annulus has suffered damage or calcification which renders it unsuitable for attachment of the valve, the invention further contemplates the reconstruction of the tissue annulus after removal of the diseased or damaged natural valve through the employment of a dynamic annulus reconstruction ring to form a suitable surface for coaptation of the free edges of the hemispheric segments of the dynamic annulus valve while allowing natural expansion and contraction of the annular ring throughout the cardiac cycle. The flexible ring of the present invention comprises an inner doughnut-shaped ring made of a rubber type material, such as silicone rubber, which is both flexible and stretchable. This inner core is covered with a fabric of suitable chemical and physical nature to provide a site for future fixation strength to the ring without restricting its movement and to provide an attachment medium for endothelial ingrowth. It is contemplated that a dynamic annulus reconstruction ring is implanted through standard suturing techniques in such a way that it creates a relatively uniform surface for coaptation of the dynamic annulus heart valve to effect closure without restricting natural annular expansion and contraction.

Fixation by this new method allows the patient's natural or reconstructed tissue annulus to flex normally throughout the cardiac cycle. Since the valve employs no metallic or rigid fabric ring around the annulus to restrict its movement, tissue ingrowth and thrombus formation should not be a complication.

The flexible membrane is attached to the flexible framework in such a manner that the membrane segments or leaflets freely open inward to allow unimpeded forward blood flow through the valve. When the cardiac cycle reverses, the leaflets bellow outward and effect closure against the tissue annulus. Because of the lack of a bulky fixation ring, this dynamic annulus valve will allow much more available area for forward blood flow and should, therefore, be superior to all other prosthetic valves in hemodynamic performance. Furthermore, the absence of a fixation ring increases the durability of the valve design. Other tissue or synthetic valve designs have had durability problems resulting, in part, from the fact that the leaflets are attached to a rigid or semi-rigid fixation ring around their perimeter. By using a central attachment without an outer fixation ring, the dynamic annulus valve effects closure by leaflet coaptation with the natural or reconstructed tissue annulus. This closing method as well as the flexibility of the structural frame should avoid localized stress points on the leaflets and result in extreme durability.

These and other attendant advantages of the invention will become better understood to those skilled in the art by reference to the following description when viewed in the light of the drawings therein:

BRIEF DESCRIPTION OF THE DRAWINGS

FIG. 1 is a perspective view of the flexible central framework of the dynamic annulus heart valve of the present invention;

FIG. 2 is a perspective view of the complete dynamic annulus heart valve of the present invention;

FIG. 3 is an axial view of the flexible central framework of a mitral dynamic nucleus heart valve of the present invention.

FIG. 4 is an axial view of the dynamic annulus heart valve in its closed condition;

FIG. 5 is an axial view of the dynamic annulus heart valve in its open condition;

DESCRIPTION OF THE PREFERRED EMBODIMENTS

Figure 6:
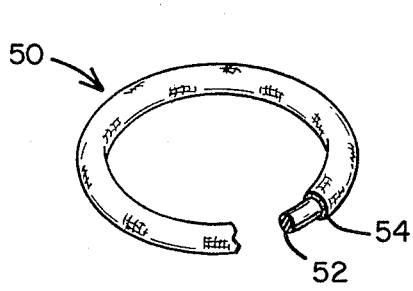
FIG. 6 is a partial perspective view of the dynamic annulus reconstruction ring of the present invention.

Referring now to FIG. 1, the valve includes a framework comprising, in this embodiment three arcuate shaped struts 10, 12 and 14 joined together at point 16 so that the free ends thereof are directed in a common direction and terminate at points extending roughly equidistantly from the common point of joinder 16. At the extremities of the struts 10, 12 and 14, are attached suture pads 18, 20 and 22, respectively. The struts, such as strut 10, may have formed at their extremities a framework (not shown) to which or over which the suture pads 18, 20 and 22 may be formed and/or may be attached.

The struts forming the framework may be made of a resilient or a springy material which is nonthrombogenic such as titanium or polytetrafluoroethylene or Teflon ® polymer. The suture pads may be formed of open mesh Dacron ® polymer (polyethylene terephthalate) cloth sewn in layers over the pad framework. Alternatively, the suture pads may be formed of expanded polytetrafluoroethylene in the form of several layers of thin sheets each aligned at 90° to one another and bonded together and to the pad framework. Other methods of forming a suitable pad from nonthrombogenic and body compatible material are disclosed in commonly assigned U.S. Pat. No. 4,197,593.

The structure depicted in FIG. 1 thus defines a valve support for the dynamic annulus heart valve of the present invention. The struts 10, 12 and 14 are approximately 0.030 inch diameter in cross section, are formed in a roughly arcuate shape, e.g. a quarter arc of a circle or half-arc of a parabola, extending roughly 90° from the point of joinder 16 to the points of attachment with the suture pads 18, 20 and 22. In an embodiment suitable for use in the aortic valve, the struts 10, 12 and 14 are joined at the common point of joinder 16 to radially extend equiangularly (at 120°) with respect to one another so that the suture pads 18, 20 and 22 are equidistant from one another and from the common point of joinder 16.

Referring to FIG. 2, the framework of FIG. 1 is depicted with the flexible membrane 30 attached to the framework. The flexible membrane 30 constitutes a thin sheet of material having a thickness of about 0.003 inches or less formed of several layers of expanded polytetrafluoroethylene sheet material bonded together, each sheet being oriented prior to bonding at approximately 60° to the direction of expansion of each adjacent sheet or similar appropriate material. The membrane 30 is formed into a hemispheric or paraboloid shape designed to fit within the corresponding shape of the framework estalished by the strut 10, 12 and 14. The membrane is attached to the struts 10, 12 and 14 at all points extending from the common point of joiner 16 to the suture pads 18, 20 and 22. The flexible membrane 30, upon attachment to the flexible framework, thus possesses three hemispheric or paraboloid segments having three free edges 32, 34 and 36 extending between the adjacent suture pads 18, 20 and 22, respectively.

In the event that the framework is constructed of the same material as the membrane, the membrane 30 may be bonded to the struts 10, 12 and 14 by application of heat, pressure, or a combination thereof. Alternatively, the hemispheric membrane 30 may be supported on a suitable fixture and the struts 10, 12 and 14 formed by building up strip layers of polytetrafluoroethylene on one or both sides of the membrane 30. Or, the heart valve may be constructed of three separate hemispherical segments which are each separately attached to the struts 10, 12 and 14 by heat, pressure and heat, or sewn about the struts. In any case, the dynamic annulus heart valve depicted in FIG. 2 constitutes a flexible central frame to which the flexible membrane is attached to form at least three valve leaflets which expand outwardly in the reverse direction of flow of blood to block passage of blood through a valve annulus and which contract inwardly against one another to allow forward flow of blood.

Thus, the completed heart valve, viewed as depicted in FIGS. 4 and 5, is circular in appearance viewed axially. In the mitral valve embodiment (shown in FIG. 3), the framework formed by struts 10, 12 and 14 would be oblong employing either three or four struts (not shown). In the four-strut embodiment, the struts would be joined at the point of joinder 16 so that the struts radially extend at 90° from one another. In the three strut, oblong embodiment (shown in FIG. 3), struts 10 and 12 can form on angle of about 160°, and the two angles between strut 14 and the other struts 10 and 12 can be at about 100° from the other two struts. In either case, the two principle struts 10 and 12 would extend in the major oblong direction and the third strut 14 (or the third and fourth struts) would extend in the minor oblong dimension. The membrane 30 is attached as described above to the strut framework.

Referring to FIG. 4, the dynamic annulus heart valve of the present invention (aortic embodiment) is depicted in the valve closed position sewn to tissue annulus 41 wherein the membrane 30 is fully expanded by flow of blood in the direction extending toward the viewer. The membrane 30 balloons out in a hemispheric or a paraboloid shape so that the edges 32, 34 and 36 contact the tissue annulus to which the suture pads 18, 20 and 22 are sutured. In reference to FIG. 5, the dynamic annulus heart valve (aortic embodiment) is depicted from the same direction but showing the flow of blood in the direction away from the viewer whereby the leaflets of the flexible membrane 30 are collapsed against one another. In FIG. 5, it can be seen that the flow of blood is impeded only by the centrally located framework, and blood flows between the tissue annulus 41 and the collapsed valve.

FIG. 6 shows, in partial cross-section, the dynamic annulus tissue reconstruction ring, 50, which is fabricated in various sizes to fit the orifice left after surgery for the removal of a valve and sewn therein. The ring 50 is composed of an inner doughnut shaped body, 52, of relaxed and pliant silicone rubber and a Dacron ® or other suitable fabric sleeve 54 surrounding the silicone rubber body 52.

The attachment of the reconstruction ring 50 to the irregularly shaped orifice is accomplished by sizing the orifice, selecting a reconstruction ring of the correct size, and suturing the ring in place to the remaining heart tissue to form an annulus, either circular or oval, depending on the valve type. Tissue ingrowth into fabric 54 will take place over time, and the relaxed silicone rubber will be capable of flexing with the expansion and contraction of the heart. Attachment of the dynamic annulus heart valve to the ring, 50, or to appropriate tissue distal to the ring will enable the efficient closure or coaptation of the free edges of the valve segments against a relatively uniform annulus in the manner described above.

Figure 7:
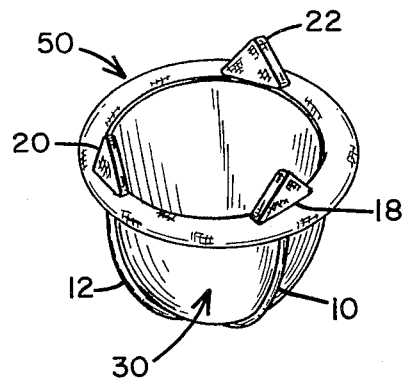
FIG. 7 is a perspective view of an assembled dynamic annulus heart valve and reconstruction ring of the present invention.

In FIG. 7, the dynamic annulus tissue reconstruction ring 50 is shown with the heart valve described above in the position of their ultimate use in the heart. When the ring 50 is surgically attached as described above, it provides a regular annulus surface for coption of the free edges of the valve segments.

Figure 8:
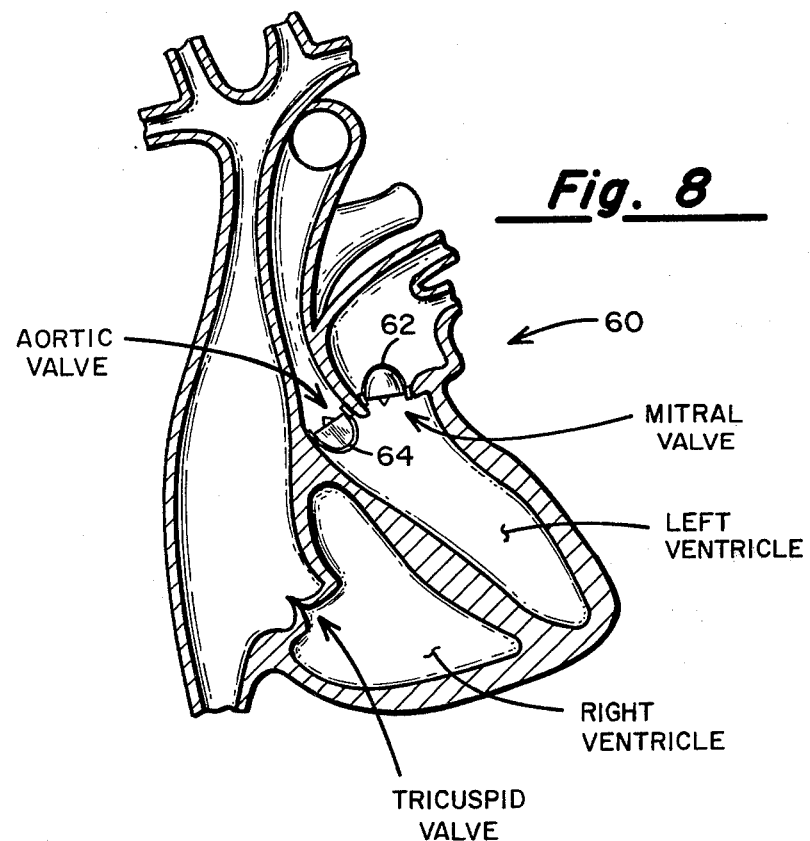
FIG. 8 is a cross-sectional view of the human heart with the dynamic annulus heart valves sutured in place in the mitral and aortic valve locations.

In reference to FIG. 8, two of the heart valves of the present invention are depicted in cross-section in the aortic and mitral valve locations of the human heart 60. The valve 62 is shown in the mitral position and is closed, and the valve 64 is shown in the aortic position and is open.

What is claimed is:
1. A prosthetic heart valve comprising:
   a. a flexible frame means comprising a plurality of arcuate frame struts, means for commonly joining together one end of each frame strut and for extending the valve struts radially and in a common direction from the point of joinder so that the free ends of said valve struts terminate at points spaced from one another and radially from said common point and each of said valve struts curves approximately 90° from said point of joinder to said free end thereof;
   b. a plurality of valve leaflets formed of thin, flexible, impermeable sheet material, each leaflet having three edges and a hemispheric segment shape, with first and second edges conforming to the hemispheric segment shape defined by two adjacent valve struts extending from said point of joinder to the free ends thereof and the third edge having a length sufficient to extend between the free ends of said two adjacent valve struts in an arc measured radially from said point of joinder;
   c. means for attaching the first and second edges of each of said valve leaflets along the length of adjacent ones of said valve struts from said point of joinder to adjacent free ends thereof, leaving the third edge extending between free ends of said valve struts; and
   d. fixation means coupled to said free ends of said valve struts for providing points of attachment of said valve to cardiac tissue; whereby said valve leaflets are adapted to bellow out and effect closure of the third edge of each of said leaflets against body tissue in a first direction of blood flow and to collapse inward against one another in a second direction of blood flow to thus block or allow blood flow in said first and second directions.

2. The heart valve of claim 1 wherein said plurality of frame struts comprises three valve struts and said commonly joining means equiangularly joins said valve struts for providing a generally circular configuration of said valve, when viewed axially, capable of use as an aortic replacement valve.

3. The heart valve of claim 1 wherein said plurality of frame struts comprises three valve struts, one of said valve struts being shorter in length than the other two valve struts, and said commonly joining means joins said one valve strut and said other two struts at a first and second vertical angle and commonly joins said other two valve struts at a third angle greater than said first and second angles for providing a generally oblong configuration of said valve, when viewed axially, capable of use as a mitral replacement valve.

4. The heart valve of claim 1 wherein said valve leaflets are formed of a single membrane shaped into a curved surface conforming to the shape of said open framework and wherein said free edges constitute segments of a single free edge of said membrane extending between adjacent free ends of said valve struts.

5. The heart valve of claim 4 wherein said valve struts and said valve leaflets are formed of a common biocompatible and non-thrombogenic material and said attaching means comprises the molecular bond of said membrane material to said valve strut material.

6. The heart valve of claim 5 wherein said material is expanded polytetrafluoroethylene sheet material and said membrane and framework is formed of bonded layers of said sheet material.

7. The heart valve of claim 1 wherein said material is expanded polytetrafluoroethylene sheet material and said membrane and framework is formed of bonded layers of said sheet material.

8. The heart valve of claim 4 wherein said material is expanded polytetrafluoroethylene sheet material and said membrane and framework is formed of bonded layers of said sheet material.

9. The heart valve of claim 1 further comprising:
an annular reconstruction ring meant for implantation in the position of the excised natural heart valve and for reconstructing an annular surface suitable for attachment of a heart valve formed of a ring-shaped body of relaxed and pliant silicone rubber with an elastic fabric sleeve surrounding said body through which said ring means may be sutured in place around the excised valve annulus.

10. A prosthetic heart valve for permanent implantation in the heart valve annulus comprising:
a. expansible valve frame means further comprising a plurality of flexible, curved valve struts and means for joining one end of each valve strut together to form a curved, open framework, the other free ends of said valve struts extending in a common direction with respect to the other and spaced from one another;
b. a like plurality of valve leaflets made of thin, flexible, impermeable sheet material, each leaflet formed to fit between adjacent ones of said valve struts and having a free edge extending in an arc between the respective free ends of said valve struts;
c. means for attaching said leaflets from the joined end to the free end of adjacent ones of said valve struts to form a fluid tight covering over said framework; and
d. support means for attaching the free ends of said valve struts to the tissue annulus, whereby said leaflets may bellow out and contact the tissue annulus during closure of said valve and may collapse inwardly against one another during opening of said valve.

11. The heart valve of claim 10 wherein said plurality of frame struts comprises three valve struts, one of said valve struts being shorter in length than the other two valve struts and said commonly joining means joins said one valve strut and said other two struts at a first and second vertical angle and commonly joins said other two valve struts at a third angle greater than said first and second angles for providing a generally oblong configuration of said valve, when viewed axially, capable of use as a mitral replacement valve.

12. The heart valve of claim 10 wherein said plurality of frame struts comprises three valve struts, and said commonly joining means equiangularly joins said valve struts for providing a generally circular configuration of said valve, when viewed axially, capable of use as an aortic replacement valve.

13. The heart valve of claim 10 wherein said valve leaflets are formed of a single membrane shaped into a curved surface conforming to the shape of said open framework and wherein said free edges constitute segments of a single free edge of said membrane extending between adjacent free ends of said valve struts.

14. The heart valve of claim 13 wherein said valve struts and said membrane are formed of a common biocompatible and non-thrombogenic material and said attaching means comprises molecular bond of said membrane material to said valve strut material.

15. The heart valve of claim 14 wherein said material is expanded polytetrafluoroethylene sheet material and said membrane and framework is formed of bonded layers of said sheet material.

16. The heart valve of claim 10 wherein said valve struts and said membrane are formed of a common biocompatible and non-thrombogenic material and said attaching means comprises molecular bond of said membrane material to said valve strut material.

17. The heart valve of claim 16 wherein said material is expanded polytetrafluoroethylene sheet material and said membrane and framework is formed of bonded layers of said sheet material.

18. The heart valve of claim 17 wherein said plurality of frame struts comprises three valve struts and said commonly joining means equiangularly joins said valve struts for providing a generally circular configuration of said valve, when viewed axially, capable of use as an aortic replacement valve.

19. The heart valve of claim 17 wherein said plurality of frame struts comprises three valve struts and one of said valve struts being shorter in length than the other two valve struts and said commonly joining means joins said one valve strut and said other two struts at a first and second vertical angle and commonly joins said other two valve struts at a third angle greater than said first and second angles for providing a generally oblong configuration of said valve, when viewed axially, capable of use as a mitral replacement valve.

* * * * *